(12) United States Patent
Chung et al.

(10) Patent No.: US 8,536,212 B2
(45) Date of Patent: Sep. 17, 2013

(54) PROTECTIVE AGENT FOR RETINAL NERVE OR OPTIC NERVE

(75) Inventors: Sookja Kim Chung, Hong Kong (CN); Stephen Chung, Hong Kong (CN); Chihiro Hibi, Nagoya (JP)

(73) Assignee: Sanwa Kagaku Kenkyusho Co., Ltd., Nagoya-Shi (JP)

( * ) Notice: Subject to any disclaimer, the term of this patent is extended or adjusted under 35 U.S.C. 154(b) by 359 days.

(21) Appl. No.: 12/517,882

(22) PCT Filed: Jan. 30, 2008

(86) PCT No.: PCT/JP2008/051338
§ 371 (c)(1),
(2), (4) Date: Mar. 17, 2010

(87) PCT Pub. No.: WO2008/093691
PCT Pub. Date: Aug. 7, 2008

(65) Prior Publication Data
US 2010/0216856 A1    Aug. 26, 2010

(30) Foreign Application Priority Data

Jan. 31, 2007    (JP) ............................... 2007-021852

(51) Int. Cl.
*A01N 43/50*    (2006.01)
(52) U.S. Cl.
USPC ......................................................... 514/389
(58) Field of Classification Search
USPC ......................................................... 514/389
See application file for complete search history.

(56) References Cited

U.S. PATENT DOCUMENTS

| | | | |
|---|---|---|---|
| 4,609,663 A | 9/1986 | York, Jr. | |
| 4,740,517 A | 4/1988 | Kurono et al. | |
| 4,966,452 A * | 10/1990 | Shields et al. | 351/219 |
| 5,212,196 A * | 5/1993 | House et al. | 514/392 |
| 6,127,367 A | 10/2000 | Beyer et al. | |
| 2005/0234531 A1* | 10/2005 | Peyman | 607/89 |
| 2007/0293556 A1 | 12/2007 | Kato et al. | |
| 2007/0299119 A1 | 12/2007 | Kakehashi et al. | |
| 2008/0255217 A1 | 10/2008 | Yabe et al. | |

FOREIGN PATENT DOCUMENTS

| | | | |
|---|---|---|---|
| CN | 1168794 A | | 12/1997 |
| EP | 0258476 | * | 9/1986 |
| EP | 0 485 219 A2 | | 5/1992 |
| EP | 0 595 183 A1 | | 5/1994 |
| EP | 0 719 556 A2 | | 7/1996 |
| EP | 0 792 643 A1 | | 9/1997 |
| EP | 1 719 774 A2 | | 11/2006 |
| EP | 1 723 956 A1 | | 11/2006 |
| JP | 04-173791 A1 | | 6/1992 |
| JP | 06-135968 A1 | | 5/1994 |
| JP | 07-242547 A1 | | 9/1995 |
| JP | 08-231549 A1 | | 9/1996 |
| JP | 11-310538 | | 11/1999 |
| JP | 11-310538 A1 | | 11/1999 |
| JP | 09-316003 A1 | | 12/2007 |
| WO | WO01/85183 | * | 11/2001 |
| WO | 2005/072066 A2 | | 8/2005 |
| WO | 2005/079792 A1 | | 9/2005 |
| WO | 2006/090699 A1 | | 8/2006 |

OTHER PUBLICATIONS

Kuniharu Mizuno, et al, Inhibitory Effects of Fidarestat on Aldose Reductase and Aldehyde Reductase Activity Evaluated by a New Method Using HPLC with Post-Column Spectrophotometric Detection, 23 Bio. Pharm. Bull. 244 (2000).*
Jithan Aukunuru, et al, Expression of Multidrug Resistance-Associated Protein (MRP) in Human Retinal Pigment Epithelial Cells and Its Interaction with BAPSG, a Novel Aldose Reductase Inhibitor, 18 Pharma. Res. 565 (2001).*
Lloyd Paul Aiello, Vascular Endothelial Growth Factor; 20th-Century Mechanisms, 21st-Century Therapies, 38 Inv. Ophthalmol. Vis. Sci. 1647 (1997).*
Evangelos Gragoudas, et al, Pegaptanib for Neovascular Age-Related Macular Degeneration, 351 N. Engl. J Med. 2805 (2004).*
W-H Lee, et al, Visual Acuity Outcomes of Vitrectomy, Focal Laser Photocoagulation, and Photodynamic Therapy in the treatment of Subfoveal Choroidal Neovascularization Arising from Age-Related Macular Degeneration, 43 IOVS 3983(2002).*
Y.H. Park, et al, Pharmacokinetics and Efficacy of Structurally Related Spirohydantoin and Spirosuccinimide Aldose Reductase Inhibitors, 22 Xenobiotica 543 (1992).*
Hiroto Shibuki, et al, Lipid Peroxidation and Peroxynitrite in Retinal Ischemia-Reperfusion Injury, 41 Invest. Ophthalmol. Vis. Sci. 3607 (2000).*

(Continued)

Primary Examiner — Sean Basquill
(74) Attorney, Agent, or Firm — Burr & Brown

(57) ABSTRACT

The present invention provides a protective agent for retinal nerve or optic nerve which exerts its effect through a different mechanism from that of conventional therapeutic agents and can be taken for long periods. The present invention is the protective agent for retinal nerve or optic nerve which comprises a compound with aldose reductase inhibiting activity such as the compound represented by the following general formula as an active ingredient. A preferable compound thereof is (2S,4S)-6-fluoro-2',5'-dioxospiro[chroman-4,4'-imidazolidine]-2-carboxamide:

[Formula 1]

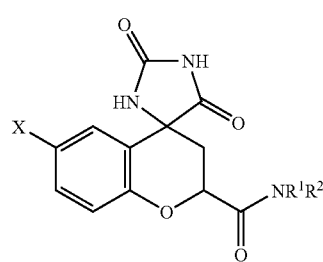

wherein X represents a halogen atom or a hydrogen atom, R1 and R2 independently represent a hydrogen atom or an optionally substituted C1 to C6 alkyl group, or $R^1$ and $R^2$, together with a nitrogen atom bound thereto, or optionally another nitrogen atom or an oxygen atom, are combined to form a 5- to 6-membered heterocycle.

18 Claims, 2 Drawing Sheets

(56) References Cited

OTHER PUBLICATIONS

M.D. Jose Pedro De La Cruz et al., "*Pharmacological Approach to Diabetic Retinopathy*," Diabetes/Metabolism Research and Reviews, Diabetes Metab. Res. Rev., vol. 20, Jan. 27, 2004, pp. 91-113.

Grant M. Comer et al., "*Current and Future Pharmacological Intervention for Diabetic Retinopathy*," Expert Opinion Emerging Drugs, vol. 10, No. 2, May 2005, pp. 441-455.

Mizuno et al., "*Continuous Inhibition of Excessive Polyot Pathway Flux in Peripheral Nerves by Aldose Reductase Inhibitor Fidarestat Leads to Improvement of Diabetic Neuropathy*," Journal of Diabetes and Its Complications, 1999; vol. 13, No. 3, pp. 141-150.

Extended European Search Report mailed Apr. 18, 2013.

Japanese Office Action, (with partial English translation) Japanese Patent Application No. P2008-556121, dated Jun. 11, 2013 (4 pages).

"The Japanese Journal of Clinical and Experimental Medicine, vol. 75 No. 6 p. 1390-1391 (1998)" (with partial English translation) (3 pages).

"Active Service for Glaucoma Part II, Tokyo Glaucoma Seminar Edition/Publication, p. 85-93 (1999)" (with partial English translation) (14 pages.).

"Gendai Iryo ("Modern Medicine"), vol. 25 No. 10 p. 143-146 (1993)" (with partial English translation) (8 pages).

"Ganka Shinryo Practice ("Ophthalmic Care Practice"), vol. 5 No. 8 p. 160-162 (2002)" (with partial English translation) (5 pages).

"Japanese Journal of Ophthalmology, vol. 106, Special Edition, p. 198 (414) (2002)" (with partial English Translation) (5 pages).

\* cited by examiner

PROTECTIVE AGENT FOR RETINAL NERVE OR OPTIC NERVE

TECHNICAL FIELD

The present invention relates to a protective agent for retinal nerve or optic nerve which comprises a compound with aldose reductase inhibiting activity as an active ingredient.

BACKGROUND ART

A variety of retinal degenerative diseases with retinal neuronal cell death are a major cause of blindness. That is, functional visual loss such as decrease in visual acuity and defect in the visual field is caused by degeneration and loss of the retina and optic nerves due to persistent or acute ocular hypertension, ischemia, and inflammation. Usually, the retina and optic nerves do not regenerate. Therefore, it is extremely difficult to regain the lost function.

Particularly, primary open-angle glaucoma is a leading cause of blindness in industrialized countries. Intraocular pressure-lowering therapy based on medication or laser trabeculoplasty has been performed. However, it is possible to slow the progression of glaucoma, but the prevention and improvement in the progress are still difficult. Particularly, acute primary angle-closure glaucoma shows rapid and high functional visual loss and has a high risk of blindness. Although early intraocular pressure-lowering therapy is performed, satisfied treatment results are currently not achieved. Recently, normal tension glaucoma has received attention because of increased morbidity. Although intraocular pressure-lowering therapy is effective in the case, prevention of progression has not been achieved. Since circumstances of the glaucomatous treatment are described above, there is a need of a novel pharmacotherapy which does not depend on intraocular pressure which is the cause of glaucoma.

The number of patients with age-related macular degeneration is increasing as the aging of society. In the treatment of exudative age-related macular degeneration, choroidal neovascular vessels are destroyed with laser beam. However, the treatment cannot be applied to the central part of the macula lutea and thus there is a need of a novel pharmacotherapy.

Further, photocoagulation is performed for branch retinal vein occlusion (BRVO), central retinal vein occlusion (CRVO), diabetic retinopathy and diabetic maculopathy. Although the proliferation of neovascular vessels is suppressed, the inflammation and circulatory disorder of retina are induced and decreased visual acuity is easily caused, which is a concern. Additionally, in vitreous surgery for severe maculopathy and severe proliferative retinopathy, a rapid ischemic reperfusion state is caused by the surgery. Visual recovery is not observed or is significantly delayed, which is bothering clinicians and patients. For these reasons, there is a need of a novel pharmacotherapy which prevents deterioration in visual function due to ophthalmic surgical treatment.

On the other hand, the present applicant has found (2S,4S)-6-fluoro-2',5'-dioxospiro[chroman-4,4'-imidazolidine]-2-carboxamide (generic name: Fidarestat), i.e, a potent aldose reductase (AR) inhibitor. The compound has been developed as a compound which ensures high safety even if it is administered over long periods. Currently, its effect as a therapeutic agent for diabetic neuropathy has been studied in clinical trials.

With reference to the hydantoin derivative including fidarestat, the application to diabetic neuropathy is described in Japanese Patent Application Laid-Open (JP-A) No. 61-200991, the application to circulatory system disease is described in JP-A No. 4-173791, the application to age-related diseases is described in JP-A No. 6-135968, the application to simple diabetic retinopathy is described in JP-A No. 7-242547, the application to diabetic keratopathy is described in JP-A No. 8-231549, the application to diabetic maculopathy is described in WO2005/072066, the application to severe diabetic retinopathy is described in WO2005/079792, and the application to impaired cardiac function or myocardial damage resulting from ischemia or ischemia reperfusion is described in WO2006/090699. However, the use of the compound as the protective agent for retinal nerve or optic nerve is completely unknown. Further, the use of other aldose reductase inhibitors as the protective agent for retinal nerve or optic nerve has not been reported.

[Patent document 1] JP-A No. 61-200991
[Patent document 2] JP-A No. 4-173791
[Patent document 3] JP-A No. 6-135968
[Patent document 4] JP-A No. 7-242547
[Patent document 5] JP-A No. 8-231549
[Patent document 6] WO2005/072066
[Patent document 7] WO2005/079792
[Patent document 8] WO2006/090699

DISCLOSURE OF THE INVENTION

Problem to be Solved by the Invention

As described above, in the preventive or therapeutic agent for functional visual loss resulting from retinal ischemia or ischemia-reperfusion injury, there is a strong need of an effective and safer therapeutic agent in clinical practice. Particularly, from the viewpoint of the safety of medical treatment and ophthalmic surgical treatment, there is a strong need of a safer pharmacotherapy which can be used over a long period of time. An objective of the present invention is to provide a protective agent for retinal nerve or optic nerve which can be taken for long periods.

The present inventors have proposed a therapeutic agent based on a new concept, i.e., a neuroprotective drug for retinal nerve or optic nerve in view of the above circumstances. The therapeutic agent has an action mechanism different from conventional drugs which secondarily protect retinal nerve or optic nerve by enhancing intraocular pressure and intraocular inflammation responsible for glaucoma. In other words, the therapeutic agent has little effect on ocular hypertension, inflammation, or thrombus which leads to retinal nerve degeneration and protects retinal nerve or optic nerve.

In the present invention, mouse models with acute ophthalmic artery occlusion, namely, mouse models with ophthalmic artery occlusion have been produced and the neuroprotective effect of the compound with aldose reductase (AR) inhibiting activity on retinal nerve or optic nerve has been evaluated. As a result, it is found that AR gene defect or the administration of the compound with aldose reductase (AR) inhibiting activity is effective for the loss of retinal ganglion cells which is caused by ischemic reperfusion in the mouse ophthalmic artery. That is, the present invention is the protective agent for retinal nerve or optic nerve which comprises the compound with aldose reductase (AR) inhibiting activity as an active ingredient.

The protective agent for retinal nerve or optic nerve of the present invention can be used, for example, as a preventive or therapeutic agent for decrease or deterioration in visual function. Here, examples of the decrease or deterioration in visual function include conditions resulting from retinal ischemia or retinal ischemia reperfusion injury in glaucoma, maculopathy, uveitis, or ocular vascular occlusion.

Further, for example, the retinal ischemia reperfusion injury is the one occurring after photocoagulation, vitreous surgery or medication for age-related macular degeneration, diabetic maculopathy, diabetic retinopathy, branch retinal vein occlusion (BRVO), or central retinal vein occlusion (CRVO), the one occurring after medication or laser trabeculoplasty for primary open-angle glaucoma or normal tension glaucoma, the one occurring after medication, laser iridotomy, or surgical iridectomy for primary angle-closure glaucoma, or the one occurring after thrombolytic therapy for refractory optic neuropathy.

As the compound with aldose reductase (AR) inhibiting activity, the hydantoin derivative represented by the following general formula is listed. A preferable example of the hydantoin derivative is (2S,4S)-6-fluoro-2',5'-dioxospiro[chroman-4,4'-imidazolidine]-2-carboxamide (generic name: Fidarestat).

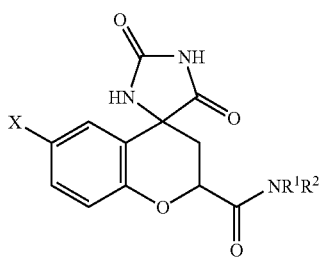

[Formula 1]

wherein X represents a halogen atom or a hydrogen atom, R1 and R2 independently represent a hydrogen atom or an optionally substituted C1 to C6 alkyl group, or $R^1$ and $R^2$, together with a nitrogen atom bound thereto, or optionally another nitrogen atom or an oxygen atom, are combined to form a 5- to 6-membered heterocycle.

Other examples of the compound with aldose reductase (AR) inhibiting activity include Ranirestat (AS-3201), ARI-809, Epalrestat, Zopolrestat, Zenarestat, Tolrestat, Imirestat, Ponalrestat, Voglistat, TAT (WP-921), M-160209, SG-210, and NZ-314.

According to another aspect of the present invention, there is provided use of the compound with aldose reductase inhibiting activity for manufacturing the protective agent for retinal nerve or optic nerve. With reference to the matter, subordinate concepts of the present invention are established as with the present invention of the above-described agent.

According to the present invention, there is provided the protective agent for retinal nerve or optic nerve which is effective against functional visual loss resulting from retinal ischemia or retinal ischemia reperfusion injury. Especially, when fidarestat is used as an aldose reductase (AR) inhibitor, the protective agent for retinal nerve or optic nerve of the present invention shows significant effects at low doses, can be administered over a long period of time, and is not problematic from a safety standpoint.

BEST MODE FOR CARRYING OUT THE INVENTION

Figure 1:
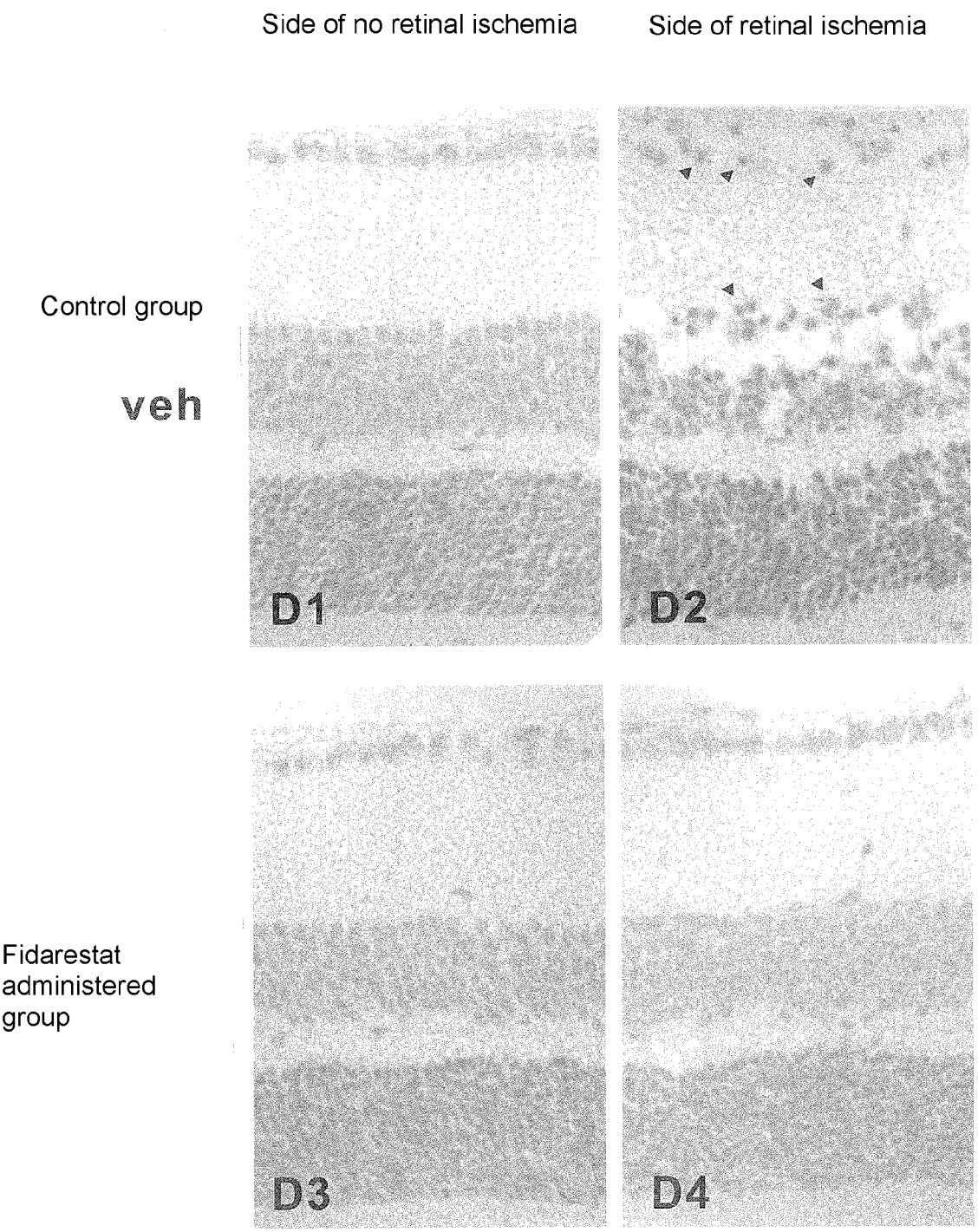
FIG. 1 shows the effect of fidarestat on retinal ganglion cell death in mouse models with ophthalmic artery occlusion.

Herein below, the present invention will be more specifically described.

The present invention is a protective agent for retinal nerve or optic nerve which comprises the compound with aldose reductase (AR) inhibiting activity as an active ingredient. The protective agent for retinal nerve or optic nerve of the present invention has, for example, a preventive or therapeutic effect for decrease or deterioration in visual function.

Here, the term "decrease or deterioration in visual function" means decrease in visual acuity or defect in the visual field. Examples thereof include conditions resulting from retinal ischemia or retinal ischemia reperfusion injury in glaucoma, maculopathy, uveitis, or ocular vascular occlusion. Examples of the glaucoma include primary open-angle glaucoma, primary angle-closure glaucoma, acute angle-closure glaucoma, secondary glaucoma (neovascular glaucoma, steroid-induced glaucoma), and developmental glaucoma. Examples of the maculopathy include retinitis pigmentosa, maculopathy accompanied by edema or neovascular vessel, and age-related macular degeneration. Examples of the cause of uveitis include Behcet's disease, Harada's disease, sarcoidosis, and unknown causes. Examples of ocular vascular occlusion include branch retinal vein occlusion (BRVO), central retinal vein occlusion (CRVO), central retinal artery occlusion (CRAO), and refractory optic neuropathy (ischemic optic neuropathy caused by circulatory disorder in the nutrient vessels of the optic nerve such as cerebral infarction or transient ischemic attack).

For example, the retinal ischemia reperfusion injury is the one occurring after photocoagulation, vitreous surgery or medication of VEGF or steroid for age-related macular degeneration, diabetic maculopathy, diabetic retinopathy, branch retinal vein occlusion (BRVO), or central retinal vein occlusion (CRVO), the one occurring after medication or laser trabeculoplasty for primary open-angle glaucoma or normal tension glaucoma, the one occurring after medication, laser iridotomy, or surgical iridectomy for primary angle-closure glaucoma, or the one occurring after thrombolytic therapy for refractory optic neuropathy.

As a compound with aldose reductase (AR) inhibiting activity, a hydantoin derivative represented by the following general formula is listed.

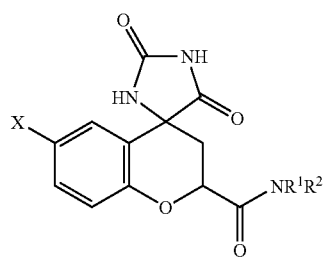

[Formula 2]

wherein X represents a halogen atom or a hydrogen atom, R1 and R2 independently represent a hydrogen atom or an optionally substituted C1 to C6 alkyl group, or $R^1$ and $R^2$, together with a nitrogen atom bound thereto, or optionally another nitrogen atom or an oxygen atom, are combined to form a 5- to 6-membered heterocycle.

In the hydantoin derivative, it is preferable that X is fluorine. It is preferable that $R^1$ and $R^2$ are hydrogen atom or C1-3 alkyl group which may be substituted. Among them, the most preferable compound is (2S,4S)-6-fluoro-2',5'-dioxospiro [chroman-4,4'-imidazolidine]-2-carboxamide (generic name: Fidarestat).

Further, other examples of the compound with aldose reductase (AR) inhibiting activity include Ranirestat (AS-3201), ARI-809, Epalrestat, Zopolrestat, Zenarestat, Tolrestat, Imirestat, Ponalrestat, Voglistat, TAT (WP-921), M-160209, SG-210, and NZ-314.

Although a protective agent for retinal nerve or optic nerve in the present invention varies depending on the compound being selected, the protective agent can be administered as oral formulations such as tablets, capsules, powders, pellets, solutions, or syrup by usual formulation techniques, or as parenteral formulations such as eye drops, injectable solutions, or suppositories. In the case of solid formulations, when formulating, pharmaceutically acceptable vehicles such as starch, lactose, sucrose, glucose, crystalline cellulose, carboxy cellulose, carboxymethyl cellulose, carboxy ethylcellulose, calcium phosphate, magnesium stearate, and gum arabic can be used. If necessary, lubricants, binders, disintegrating agents, coating agents, coloring agents, and the like can be mixed therewith. Alternatively, in the case of liquid formulation, stabilizers, dissolving aids, suspending agents, emulsifying agents, buffer agents, preservatives, and the like can be used.

The dosage administered will vary depending upon the compound to be selected, symptoms, age, mode of administration, dosage form, and the like. In the usual case, the dosage of the above-mentioned compound is in the range of 0.1 to 200 mg/day, more preferably 1 to 100 mg/day in adults, which can be administered in one dose or the dose can be split into several doses on a daily basis. The above description is most suitable for, particularly the case where fidarestat is used as the aldose reductase (AR) inhibitor.

EXAMPLES

1. Test Method

In the experiment, mouse models with acute ophthalmic artery infarction, namely, mouse models with ophthalmic artery infarction were used. In Experiment 1, eight to ten-week-old C57BL/6N normal mice (wild type mice) were used and the therapeutic efficacy of fidarestat as the compound with aldose reductase (AR) inhibiting activity was evaluated. Here, those mice were divided into two groups: a control group to which only vehicle was administered and a fidarestat administered group to which fidarestat was administered. In Experiment 2, eight to ten-week-old C57BL/6N normal mice (wild type mice:$AR^{+/+}$ mice) and AR gene-deficient mice ($AR^{-/-}$ mice) were used and the role of AR was examined. Here, those mice were divided into two groups: a wild type mouse group ($AR^{+/+}$ mice) and an AR gene-deficient mouse group ($AR^{-/-}$ mice) and a drug administered group was not used.

Used mice (24 to 28 g of body weight) were subjected to intraluminal suture with nylon monofilament under gas anesthesia. A nylon filament was inserted into the right internal carotid artery at the bifurcation of the middle cerebral artery and the anterior cerebral artery from the common carotid artery. The mice were subjected to retinal ischemia in the right eye. The filament was pulled 2 hours after the ischemia and reperfusion was performed for 22 hours. On the other hand, left eye was evaluated as a normal control eye. In order to confirm ischemia or reperfusion, relative cerebral blood flow (rCBF) in the middle cerebral artery was monitored with a laser Doppler meter during the experiment. Decrease in the rCBF of 75% or more was defined as middle cerebral artery ischemia. The drug was administered 15 minutes before reperfusion starts by forced intragastric administration. At the end of the experiment, the isolated eyes were fixed in 4% paraformaldehyde at 4° C. overnight. The retinal ganglion cell layer was subjected to hematoxylin and eosin stain. Then, the number of surviving retinal ganglion cells was observed and measured. In this regard, cells which showed pyknotic nuclei were defined as non-surviving cells. All cells of the retina ganglionic layer in each retina section were measured. Further, all measurements were performed by a blind fashion.

2. Results (1) Pathological Findings of Survival of Retinal Ganglion Cells

Experiment 1

When retinal ischemia was performed for 2 hours, followed by ischemia reperfusion for 22 hours, the finding showing retinal ganglion cell death (indicated by black arrows) was observed in the side of retinal ischemia in the control group (FIG. 1: D2). However, in the side of no retinal ischemia, the finding showing retinal ganglion cell death was not observed (FIG. 1: D1). On the other hand, the finding showing retinal ganglion cell death was not observed in the side of retinal ischemia or the side of no retinal ischemia in the fidarestat administered group (FIG. 1: D3, D4).

Experiment 2

Figure 2:
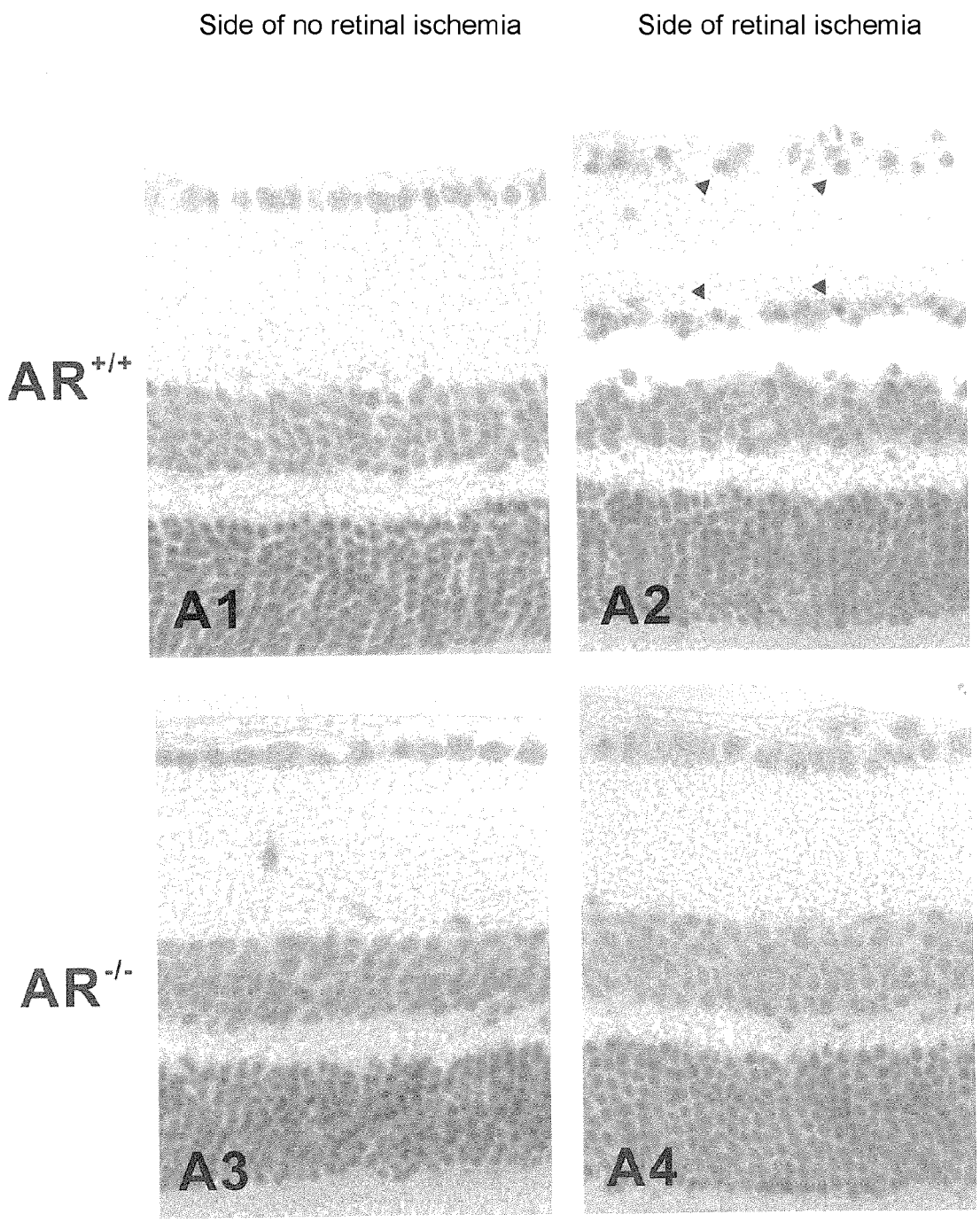
FIG. 2 shows the effect of AR gene-deficient mice on retinal ganglion cell death in mouse models with ophthalmic artery occlusion.

In the side of retinal ischemia in the wild type mouse group, the finding showing retinal ganglion cell death was observed (FIG. 2: A2). However, the finding showing retinal ganglion cell death was not observed in the side of retinal ischemia in the AR gene-deficient mouse group (FIG. 2: A4). On the other hand, as for the side of no retinal ischemia in both mouse groups, the finding showing retinal ganglion cell death was not observed (FIG. 2: A1, A3).

(2) The Number of Surviving Retinal Ganglion Cells

Experiment 1

Results are shown in Table 1. The number of surviving retinal ganglion cells present on the side of retinal ischemia in the control group was significantly decreased as compared with that on the side of no retinal ischemia ($P<0.001$). On the other hand, the number of surviving retinal ganglion cells present on the side of retinal ischemia in the fidarestat administered group was significantly increased as compared with that in the control group ($P<0.001$). As for the side of no retinal ischemia, difference in the number of surviving retinal ganglion cells in the fidarestat administered group and the control group was not observed.

TABLE 1

Effect of fidarestat on the number of surviving retinal ganglion cells

|  | Side of no retinal ischemia | Side of retinal ischemia |
|---|---|---|
| Control group | 24 ± 1 | 4 ± 1*** |
| Fidarestat administered group | 23 ± 1 | 21 ± 1††† |

The number of surviving retinal ganglion cells per 1 μm of retina section, average ± SEM
***$P < 0.001$: Side of retinal ischemia vs side of no retinal ischemia in the control group
†††$P < 0.001$: Side of retinal ischemia in the fidarestat administered group vs side of retinal ischemia in the control group

Experiment 2

Results are shown in Table 2. The number of surviving retinal ganglion cells present on the side of retinal ischemia in the wild type mouse group was significantly decreased as compared with that on the side of no retinal ischemia (P<0.001). On the other hand, the number of surviving retinal ganglion cells present on the side of retinal ischemia in the AR gene-deficient mouse group was significantly increased as compared with that in the wild type mouse group (P<0.001). As for the side of no retinal ischemia, difference in the number of surviving retinal ganglion cells in the wild-type mouse group and the AR gene-deficient mouse group was not observed.

TABLE 2

Effect of AR gene-deficient mice on the number of surviving retinal ganglion cells

|  | Side of no retinal ischemia | Side of retinal ischemia |
| --- | --- | --- |
| Wild-type mice | 23 ± 1 | 3 ± 1*** |
| AR gene-deficient mice | 21 ± 3 | 18 ± 2†† |

The number of surviving retinal ganglion cells per 1 μm of retina section, average ± SEM
***P < 0.001: Side of retinal ischemia vs side of no retinal ischemia in the wild-type mice
††P < 0.01: Side of retinal ischemia in the wild-type mice vs side of retinal ischemia in the AR gene-deficient mice

3. Discussion

Retinal ganglion cells play a critical role in photoreception and neurotransmission in the retina. It is believed that the degeneration or loss of retinal ganglion cells causes visual function damage such as decrease in visual acuity and defect in the visual field. This time, the effect of fidarestat on retinal ganglion cells and the effect of AR gene defect were examined using mouse models with acute ophthalmic artery occlusion, namely, mouse models with ophthalmic artery occlusion. As a result, fidarestat showed remarkable effectiveness against retinal ganglion cell death after retinal ischemia reperfusion and reduction in the number of surviving retinal ganglion cells. Further, the effect was almost equal to that of the AR gene defect.

These results show that the aldose reductase (AR) inhibitor such as fidarestat is effective for protecting the retina and/or optic nerve from cell degeneration or cell loss of the retina nerve and/or optic nerve which is caused by chronic or acute retinal ischemia or retinal ischemia reperfusion injury in glaucoma, maculopathy, uveitis, or ocular vascular occlusion. In other words, it is suggested that the aldose reductase (AR) inhibitor such as fidarestat has a preventive or therapeutic effect for decrease or deterioration in visual function such as decrease in visual acuity or defect in the visual field which is caused by cell degeneration or cell dropout of the retina nerve and/or optic nerve.

The invention claimed is:

1. A method for preventing or minimizing a decrease or deterioration in visual function in a patient with a condition selected from the group consisting of glaucoma, retinitis pigmentosa, age-related macular degeneration, uveitis, and ocular vascular occlusion, comprising administering to said patient an effective amount of (2S,4S)-6-fluoro-2',5'-dioxospiro[chroman-4,4'-imidazolidine]-2-carboxamide.

2. The method according to claim 1,
wherein the condition is age-related macular degeneration.

3. The method according to claim 2,
wherein the decrease or deterioration in visual function resulting from age-related macular degeneration is the one occurring after photocoagulation or vitreous surgery for age-related macular degeneration.

4. The method according to claim 3,
wherein the decrease or deterioration in visual function resulting from age-related macular degeneration is the one occurring after photocoagulation for age-related macular degeneration.

5. The method according to claim 3,
wherein the decrease or deterioration in visual function resulting from age-related macular degeneration is the one occurring after vitreous surgery for age-related macular degeneration.

6. The method according to claim 1,
wherein the non-diabetic ocular disorder is ocular vascular occlusion.

7. The method according to claim 6,
wherein the ocular vascular occlusion is selected from the group consisting of branch retinal vein occlusion (BRVO), central retinal vein occlusion (CRVO), central retinal artery occlusion (CRAO), and refractory optic neuropathy.

8. The method according to claim 7,
wherein the ocular vascular occlusion is branch retinal vein occlusion (BRVO) or central retinal vein occlusion (CRVO).

9. The method according to claim 8,
wherein the decrease or deterioration in visual function resulting from ocular vascular occlusion is the one occurring after photocoagulation or vitreous surgery for branch retinal vein occlusion (BRVO).

10. The method according to claim 8,
wherein the decrease or deterioration in visual function resulting from ocular vascular occlusion is the one occurring after photocoagulation or vitreous surgery for central retinal vein occlusion (CRVO).

11. The method according to claim 6,
wherein the decrease or deterioration in visual function resulting from ocular vascular occlusion is the one occurring after thrombolytic therapy for refractory optic neuropathy.

12. The method according to claim 1,
wherein the condition is glaucoma.

13. The method according to claim 12,
wherein the glaucoma is selected from the group consisting of primary open angle glaucoma, primary angle closure glaucoma, acute angle-closure glaucoma, secondary glaucoma, developmental glaucoma and normal tension glaucoma.

14. The method according to claim 13,
wherein the decrease or deterioration in visual function resulting from glaucoma is the one occurring after laser trabeculoplasty for primary open angle glaucoma.

15. The method according to claim 13,
wherein the decrease or deterioration in visual function resulting from glaucoma is the one occurring after laser trabeculoplasty for normal tension glaucoma.

16. The method according to claim 13,
wherein the decrease or deterioration in visual function resulting from glaucoma is the one occurring after laser iridotomy or surgical iridectomy for primary angle-closure glaucoma.

17. The method according to claim 1,
wherein the non-diabetic ocular disorder is retinitis pigmentatosa.

18. The method according to claim 1,
wherein the non-diabetic ocular disorder is uveitis.

* * * * *